(12) United States Patent
Schroeder et al.

(10) Patent No.: US 6,723,038 B1
(45) Date of Patent: Apr. 20, 2004

(54) METHODS AND DEVICES FOR IMPROVING MITRAL VALVE FUNCTION

(75) Inventors: Richard F. Schroeder, Fridley, MN (US); Robert M. Vidlund, Maplewood, MN (US); Jason E. Kalgreen, Plymouth, MN (US); Cyril J. Schweich, Jr., St. Paul, MN (US); Todd J. Mortier, Minneapolis, MN (US)

(73) Assignee: Myocor, Inc., Maple Grove, MN (US)

( * ) Notice: Subject to any disclaimer, the term of this patent is extended or adjusted under 35 U.S.C. 154(b) by 0 days.

(21) Appl. No.: 09/680,435

(22) Filed: Oct. 6, 2000

(51) Int. Cl.[7] ............................................... A61M 1/12
(52) U.S. Cl. ..................................................... 600/16
(58) Field of Search .............................. 600/16–18, 37, 600/437, 443, 445, 449, 450; 601/11, 153; 623/3.11, 1.24, 1.26, 2.14, 2.36, 2.37; 128/897

(56) References Cited

U.S. PATENT DOCUMENTS

| | | |
|---|---|---|
| 3,019,790 A | 2/1962 | Militana |
| 3,980,086 A | 9/1976 | Kletschka et al. |
| 4,192,293 A | 3/1980 | Asrican ........................... 128/1 |
| 4,261,342 A | 4/1981 | Aranguren Duo .............. 128/1 |
| 4,300,564 A | 11/1981 | Furihata |
| 4,372,293 A | 2/1983 | Vijil-Rosales ................... 128/1 |
| 4,409,974 A | 10/1983 | Freedland ...................... 128/92 |
| 4,536,893 A | 8/1985 | Parravicini ...................... 623/3 |
| 4,690,134 A | 9/1987 | Snyders |
| 4,705,040 A | 11/1987 | Mueller et al. |
| 4,936,857 A | 6/1990 | Kulik ............................. 623/3 |
| 4,944,753 A | 7/1990 | Burgess et al. ............... 623/16 |
| 4,960,424 A | 10/1990 | Grooters ......................... 623/2 |
| 4,997,431 A | 3/1991 | Isner et al. .................... 606/15 |
| 5,104,407 A | 4/1992 | Lam et al. |
| 5,106,386 A | 4/1992 | Isner et al. .................... 606/15 |

(List continued on next page.)

FOREIGN PATENT DOCUMENTS

| | | |
|---|---|---|
| DE | 36 14 292 | 11/1987 |
| DE | 42 34 127 | 5/1994 |

(List continued on next page.)

OTHER PUBLICATIONS

US 6,197,052, 3/2001, Cosgrove et al. (withdrawn)
McCarthy, Transcription of Mar. 13, 2000 Presentation by Patrick McCarthy at the American College of Cardiology.
Batista, MD et al., "Partial Left Ventriculectomy to Treat End–Stage Heart Disease", *Ann. Thorac. Surg.*, 64:634–8, 1997.

(List continued on next page.)

*Primary Examiner*—Jeffrey R. Jastrzab
*Assistant Examiner*—Frances P. Oropeza
(74) *Attorney, Agent, or Firm*—Finnegan, Henderson, Farabow, Garrett & Dunner, LLP

(57) ABSTRACT

Devices and related methods for treating heart conditions, including, for example, dilatation, valve incompetencies, including mitral valve leakage, and other heart failure conditions, may operate to assist in the apposition of heart valve leaflets to improve valve function. A method for improving the function of a valve of a heart includes placing an elongate member transverse a heart chamber so that each end of the elongate member extends through a wall of the heart, and placing first and second anchoring members external the chamber. The first and second anchoring members are attached to first and second ends of the elongate member to fix the elongate member in a position across the chamber so as to reposition papillary muscles within the chamber. A method of treating the valve may include real-time monitoring the valve function and adjusting the device based on data obtained during the real-time monitoring.

14 Claims, 9 Drawing Sheets

U.S. PATENT DOCUMENTS

| | | | |
|---|---|---|---|
| 5,131,905 A | 7/1992 | Grooters | 600/16 |
| RE34,021 E | 8/1992 | Mueller et al. | 604/51 |
| 5,169,381 A | 12/1992 | Snyders | 600/16 |
| 5,192,314 A | 3/1993 | Daskalakis | 623/3 |
| 5,250,049 A | 10/1993 | Michael | 606/12 |
| 5,284,488 A | 2/1994 | Sideris | 606/213 |
| 5,300,087 A | 4/1994 | Knoepfler | |
| 5,360,444 A | 11/1994 | Kusuhara | |
| 5,385,528 A | 1/1995 | Wilk | 680/18 |
| 5,417,709 A | 5/1995 | Slater | |
| 5,433,727 A | 7/1995 | Sideris | 606/213 |
| 5,450,860 A * | 9/1995 | O'Connor | 128/898 |
| 5,452,733 A | 9/1995 | Sterman et al. | 128/898 |
| 5,458,574 A | 10/1995 | Machold et al. | 604/101 |
| 5,496,305 A | 3/1996 | Kittrell et al. | 606/15 |
| 5,509,428 A | 4/1996 | Dunlop | 128/898 |
| 5,533,958 A | 7/1996 | Wilk | 600/18 |
| 5,571,215 A | 11/1996 | Sterman et al. | 623/66 |
| 5,584,803 A | 12/1996 | Stevens et al. | 604/4 |
| 5,593,424 A | 1/1997 | Northrup III | 606/232 |
| 5,665,092 A | 9/1997 | Mangiardi et al. | |
| 5,682,906 A | 11/1997 | Sterman et al. | 128/898 |
| 5,702,343 A | 12/1997 | Alferness | 606/37 |
| 5,713,954 A | 2/1998 | Rosenberg et al. | |
| 5,718,725 A | 2/1998 | Sterman et al. | 623/2 |
| 5,755,783 A | 5/1998 | Stobie et al. | |
| 5,758,663 A | 6/1998 | Wilk et al. | |
| 5,800,334 A | 9/1998 | Wilk | 600/18 |
| 5,800,528 A | 9/1998 | Lederman et al. | 623/3 |
| 5,800,531 A | 9/1998 | Cosgrove et al. | |
| 5,814,097 A | 9/1998 | Sterman et al. | 623/2 |
| 5,849,005 A | 12/1998 | Garrison et al. | 606/1 |
| 5,855,601 A | 1/1999 | Bessler et al. | |
| 5,855,614 A | 1/1999 | Stevens et al. | 623/11 |
| 5,865,791 A | 2/1999 | Whayne et al. | 604/49 |
| 5,902,229 A | 5/1999 | Tsitlik et al. | |
| 5,928,281 A | 7/1999 | Huynh et al. | |
| 5,944,738 A | 8/1999 | Amplatz et al. | |
| 5,957,977 A | 9/1999 | Melvin | 623/3 |
| 5,961,440 A | 10/1999 | Schweich, Jr. et al. | 600/16 |
| 5,961,549 A | 10/1999 | Nguyen et al. | |
| 5,967,990 A * | 10/1999 | Thierman et al. | 600/459 |
| 5,971,910 A | 10/1999 | Tsitlik et al. | |
| 5,971,911 A | 10/1999 | Wilk | |
| 5,972,022 A | 10/1999 | Huxel | |
| 5,972,030 A | 10/1999 | Garrison et al. | |
| 5,984,857 A | 11/1999 | Buck et al. | 600/16 |
| 5,984,917 A | 11/1999 | Fleischman et al. | |
| 6,001,126 A | 12/1999 | Nguyen-Thien-Nhon | |
| 6,019,722 A | 2/2000 | Spence et al. | |
| 6,024,096 A | 2/2000 | Buckberg | 128/898 |
| 6,024,756 A | 2/2000 | Huebsch et al. | 606/213 |
| 6,045,497 A | 4/2000 | Schweich, Jr. et al. | 600/16 |
| 6,050,936 A | 4/2000 | Schweich, Jr. et al. | 600/37 |
| 6,059,715 A | 5/2000 | Schweich, Jr. et al. | 600/16 |
| 6,071,303 A | 6/2000 | Laufer | 607/96 |
| 6,077,214 A | 6/2000 | Mortier et al. | 600/16 |
| 6,077,218 A | 6/2000 | Alferness | 600/37 |
| 6,079,414 A | 6/2000 | Roth | 128/898 |
| 6,085,754 A | 7/2000 | Alferness et al. | 128/898 |
| 6,086,532 A | 7/2000 | Panescu et al. | |
| 6,095,968 A | 8/2000 | Snyders | |
| 6,102,944 A | 8/2000 | Huynh et al. | |
| 6,110,100 A | 8/2000 | Talpade | 600/37 |
| 6,117,159 A | 9/2000 | Huebsch et al. | 606/213 |
| 6,123,662 A | 9/2000 | Alferness et al. | 600/37 |
| 6,125,852 A * | 10/2000 | Stevens et al. | 128/898 |
| 6,126,590 A | 10/2000 | Alferness | 600/37 |
| 6,132,438 A | 10/2000 | Fleischman et al. | |
| 6,143,025 A | 11/2000 | Stobie et al. | |
| 6,155,968 A | 12/2000 | Wilk | 600/16 |
| 6,155,972 A | 12/2000 | Nauertz et al. | 600/37 |
| 6,162,168 A | 12/2000 | Schweich, Jr. et al. | 600/16 |
| 6,165,119 A | 12/2000 | Schweich, Jr. et al. | 600/16 |
| 6,165,120 A | 12/2000 | Schweich, Jr. et al. | 600/16 |
| 6,165,121 A | 12/2000 | Alferness | 600/37 |
| 6,165,122 A | 12/2000 | Alferness | 600/37 |
| 6,165,183 A | 12/2000 | Kuehn et al. | |
| 6,169,922 B1 | 1/2001 | Alferness et al. | 600/37 |
| 6,174,279 B1 | 1/2001 | Girard | |
| 6,179,791 B1 | 1/2001 | Krueger | |
| 6,182,664 B1 | 2/2001 | Cosgrove | |
| 6,183,512 B1 * | 2/2001 | Howanec, Jr. et al. | 623/2.36 |
| 6,190,408 B1 * | 2/2001 | Melvin | 623/3.1 |
| 6,193,648 B1 | 2/2001 | Krueger | |
| 6,197,053 B1 | 3/2001 | Cosgrove et al. | |
| 6,206,820 B1 | 3/2001 | Kazi et al. | |
| 6,210,432 B1 | 4/2001 | Solem et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,231,561 B1 | 5/2001 | Frazier et al. | |
| 6,231,602 B1 | 5/2001 | Carpentier et al. | |
| 6,238,334 B1 | 5/2001 | Easterbrook, III et al. | |
| 6,241,654 B1 | 6/2001 | Alferness | |
| 6,245,102 B1 | 6/2001 | Jayaraman | |
| 6,245,105 B1 | 6/2001 | Nguyen et al. | |
| 6,250,308 B1 | 6/2001 | Cox | |
| 6,251,061 B1 | 6/2001 | Hastings et al. | |
| 6,258,021 B1 | 7/2001 | Wilk | |
| 6,260,820 B1 | 7/2001 | Chowdhury | |
| 6,261,222 B1 | 7/2001 | Schweich, Jr. et al. | |
| 6,264,602 B1 | 7/2001 | Mortier et al. | |
| 6,269,819 B1 | 8/2001 | Oz et al. | |
| 6,283,993 B1 | 9/2001 | Cosgrove et al. | |
| 6,290,674 B1 | 9/2001 | Roue et al. | |
| 6,293,906 B1 | 9/2001 | Vanden Hoek et al. | |
| 6,312,447 B1 | 11/2001 | Grimes | |
| 6,314,322 B1 | 11/2001 | Rosenberg | |
| 6,328,727 B1 | 12/2001 | Frazier et al. | |
| 6,331,157 B2 | 12/2001 | Hancock | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,343,605 B1 | 2/2002 | Lafontaine | |
| 6,360,749 B1 | 3/2002 | Jayaraman | |
| 6,370,429 B1 | 4/2002 | Alferness et al. | |
| 6,375,608 B1 | 4/2002 | Alferness | |
| 6,379,366 B1 | 4/2002 | Fleischman et al. | |
| 6,402,679 B1 | 6/2002 | Mortier et al. | |
| 6,402,680 B2 | 6/2002 | Mortier et al. | |
| 6,402,781 B1 | 6/2002 | Langberg et al. | |
| 6,406,420 B1 * | 6/2002 | McCarthy et al. | 600/16 |
| 6,406,422 B1 | 6/2002 | Landesberg | |
| 6,409,759 B1 | 6/2002 | Peredo | |
| 6,409,760 B1 | 6/2002 | Melvin | |
| 6,416,459 B1 | 7/2002 | Haindl | |
| 6,419,669 B1 | 7/2002 | Frazier et al. | |
| 6,425,856 B1 | 7/2002 | Shapland et al. | |
| 6,432,039 B1 | 8/2002 | Wardle | |
| 6,436,088 B2 | 8/2002 | Frazier et al. | |
| 6,439,237 B1 | 8/2002 | Buckberg et al. | |
| 6,450,171 B1 | 9/2002 | Buckberg et al. | |
| 6,458,100 B2 | 10/2002 | Roue et al. | |
| 6,461,366 B1 | 10/2002 | Seguin | |
| 6,482,146 B1 | 11/2002 | Alferness et al. | |
| 6,494,825 B1 | 12/2002 | Talpade | |
| 6,508,756 B1 | 1/2003 | Kung et al. | |

| | | | | | |
|---|---|---|---|---|---|
| 6,511,426 B1 * | 1/2003 | Hossack et al. ............ 600/437 | 2003/0181928 A1 | 9/2003 | Vidlund et al. |
| 6,514,194 B2 | 2/2003 | Schweich, Jr. et al. | | | |
| 6,520,904 B1 | 2/2003 | Melvin | FOREIGN PATENT DOCUMENTS | | |
| 6,537,198 B1 | 3/2003 | Vidlund et al. | DE | 296 19 294 | 8/1997 |
| 6,537,203 B1 | 3/2003 | Alferness et al. | DE | 199 47 885 | 4/2000 |
| 6,537,314 B2 | 3/2003 | Langberg et al. | DE | 199 47 885 A1 | 4/2000 |
| 6,544,167 B2 | 4/2003 | Buckberg et al. | DE | 298 24 017 U1 | 6/2000 |
| 6,572,529 B2 | 6/2003 | Wilk | EP | 0 583 012 | 2/1994 |
| 6,589,160 B2 | 7/2003 | Schweich, Jr. et al. | EP | 0 820 729 A1 | 1/1998 |
| 6,622,730 B2 | 9/2003 | Ekvall et al. | EP | 1 129 736 A1 | 9/2001 |
| 6,629,921 B1 | 10/2003 | Schweich, Jr. et al. | EP | 1 129 736 | 9/2001 |
| 2001/0003986 A1 | 6/2001 | Cosgrove | WO | 91/19465 | 12/1991 |
| 2001/0005787 A1 | 6/2001 | Oz et al. | WO | 95/06447 | 3/1995 |
| 2001/0009976 A1 | 7/2001 | Panescu et al. | WO | 95/16476 | 6/1995 |
| 2001/0014800 A1 | 8/2001 | Frazier et al. | WO | 96/04852 | 2/1996 |
| 2001/0014811 A1 | 8/2001 | Hussein | WO | 96/40356 | 12/1996 |
| 2001/0018611 A1 | 8/2001 | Solem et al. | WO | WO 97/14286 | 4/1997 |
| 2001/0021874 A1 | 9/2001 | Carpentier et al. | WO | 97/24082 | 7/1997 |
| 2001/0029314 A1 | 10/2001 | Alferness et al. | WO | 97/24083 | 7/1997 |
| 2001/0034551 A1 | 10/2001 | Cox | WO | 97/24101 | 7/1997 |
| 2001/0037123 A1 | 11/2001 | Hancock | WO | 98/03213 | 1/1998 |
| 2001/0039434 A1 | 11/2001 | Frazier et al. | WO | 98/14136 | 4/1998 |
| 2001/0039435 A1 | 11/2001 | Roue et al. | WO | 98/17347 | 4/1998 |
| 2001/0039436 A1 | 11/2001 | Frazier et al. | WO | 98/18393 | 5/1998 |
| 2001/0041821 A1 | 11/2001 | Wilk | WO | 98/26738 | 6/1998 |
| 2001/0041914 A1 | 11/2001 | Frazier et al. | WO | 98/29041 | 7/1998 |
| 2001/0041915 A1 | 11/2001 | Roue et al. | WO | 98/32382 | 7/1998 |
| 2001/0044568 A1 | 11/2001 | Langberg et al. | WO | WO 98/58598 | 12/1998 |
| 2001/0047122 A1 | 11/2001 | Vanden Hoek et al. | WO | 99/00059 | 1/1999 |
| 2001/0049492 A1 | 12/2001 | Frazier et al. | WO | 99/11201 | 3/1999 |
| 2002/0007216 A1 | 1/2002 | Melvin | WO | 99/16350 | 4/1999 |
| 2002/0013571 A1 | 1/2002 | Goldfarb et al. | WO | 99/22784 | 5/1999 |
| 2002/0016628 A1 | 2/2002 | Langberg et al. | WO | 99/30647 | 6/1999 |
| 2002/0019580 A1 | 2/2002 | Lau et al. | WO | 99/44534 | 9/1999 |
| 2002/0022880 A1 | 2/2002 | Melvin | WO | 99/44680 | 9/1999 |
| 2002/0026092 A1 | 2/2002 | Buckberg et al. | WO | WO 99/44969 | 9/1999 |
| 2002/0028981 A1 | 3/2002 | Lau et al. | WO | 99/52470 | 10/1999 |
| 2002/0029783 A1 | 3/2002 | Stevens et al. | WO | 99/53977 | 10/1999 |
| 2002/0032364 A1 | 3/2002 | Lau et al. | WO | 99/56655 | 11/1999 |
| 2002/0042554 A1 | 4/2002 | Alferness et al. | WO | 99/66969 | 12/1999 |
| 2002/0045798 A1 | 4/2002 | Lau et al. | WO | 00/02500 | 1/2000 |
| 2002/0045799 A1 | 4/2002 | Lau et al. | WO | 00/03759 | 1/2000 |
| 2002/0045800 A1 | 4/2002 | Lau et al. | WO | 00/06026 | 2/2000 |
| 2002/0052538 A1 | 5/2002 | Lau et al. | WO | 00/06028 | 2/2000 |
| 2002/0056461 A1 | 5/2002 | Jayaraman | WO | 00/13722 | 3/2000 |
| 2002/0058855 A1 | 5/2002 | Schweich, Jr. et al. | WO | 00/18320 | 4/2000 |
| 2002/0065449 A1 | 5/2002 | Wardle | WO | 00/25842 | 5/2000 |
| 2002/0065465 A1 | 5/2002 | Panescu et al. | WO | 00/25853 | 5/2000 |
| 2002/0077532 A1 | 6/2002 | Gannoe et al. | WO | 00/27304 | 5/2000 |
| 2002/0091296 A1 | 7/2002 | Alferness | WO | 00/28912 | 5/2000 |
| 2002/0103511 A1 | 8/2002 | Alferness et al. | WO | 00/28918 | 5/2000 |
| 2002/0111533 A1 | 8/2002 | Melvin | WO | 00/36995 | 6/2000 |
| 2002/0111636 A1 | 8/2002 | Fleischman et al. | WO | 00/42919 | 7/2000 |
| 2002/0133055 A1 | 9/2002 | Haindl | WO | 00/42950 | 7/2000 |
| 2002/0143250 A1 | 10/2002 | Panescu et al. | WO | 00/42951 | 7/2000 |
| 2002/0151766 A1 | 10/2002 | Shapland et al. | WO | 00/45735 | 8/2000 |
| 2002/0151961 A1 | 10/2002 | Lashinski et al. | WO | 00/60995 | 10/2000 |
| 2002/0161275 A1 | 10/2002 | Schweich, Jr. et al. | WO | 00/61033 | 10/2000 |
| 2002/0169358 A1 | 11/2002 | Mortier et al. | WO | 00/62715 | 10/2000 |
| 2002/0169359 A1 | 11/2002 | McCarthy et al. | WO | 00/62727 | 10/2000 |
| 2002/0173694 A1 | 11/2002 | Mortier et al. | WO | 01/00111 | 1/2001 |
| 2003/0004396 A1 | 1/2003 | Vanden Hock et al. | WO | 01/03608 | 1/2001 |
| 2003/0023132 A1 | 1/2003 | Melvin et al. | WO | 01/19291 | 3/2001 |
| 2003/0028077 A1 | 2/2003 | Alferness et al. | WO | 01/19292 | 3/2001 |
| 2003/0032979 A1 | 2/2003 | Mortier et al. | WO | 01/21070 | 3/2001 |
| 2003/0045771 A1 | 3/2003 | Schweich, Jr. et al. | WO | 01/21098 | 3/2001 |
| 2003/0045776 A1 | 3/2003 | Alferness et al. | WO | 01/21099 | 3/2001 |
| 2003/0050529 A1 | 3/2003 | Vidlund et al. | WO | 01/21247 A1 | 3/2001 |
| 2003/0065248 A1 | 4/2003 | Lau et al. | WO | 01/26557 | 4/2001 |
| 2003/0166992 A1 | 9/2003 | Schweich, Jr. et al. | WO | 01/28432 | 4/2001 |
| 2003/0171641 A1 | 9/2003 | Schweich, Jr. et al. | WO | 01/49217 A2 | 7/2001 |

| | | |
|---|---|---|
| WO | 01/50981 | 7/2001 |
| WO | 01/54562 A2 | 8/2001 |
| WO | 01/54618 | 8/2001 |
| WO | 01/54745 | 8/2001 |
| WO | 01/67985 | 9/2001 |
| WO | 01/70116 A1 | 9/2001 |
| WO | WO 01/78625 A1 | 10/2001 |
| WO | 01/85061 | 11/2001 |
| WO | 01/91667 | 12/2001 |
| WO | 01/95830 | 12/2001 |
| WO | 01/95831 | 12/2001 |
| WO | 01/95832 | 12/2001 |
| WO | 02/11625 A2 | 2/2002 |
| WO | 02/13726 A2 | 2/2002 |
| WO | 02/19917 A1 | 3/2002 |
| WO | 02/28450 A2 | 4/2002 |
| WO | 02/30292 A1 | 4/2002 |
| WO | 02/30335 A2 | 4/2002 |
| WO | 02/076284 A2 | 10/2002 |

OTHER PUBLICATIONS

Melvin, DB, "Ventricular Radius–Reduction Without Resection, A Computational Assessment", undated.

Melvin et al., "Reduction of Ventricular Wall Tensile Stress by Geometric Remodeling Device," 1 page, undated.

Melvin, DB et al., "Reduction of Ventricular Wall Tensile Stress by Geometric Remodeling Device," Poster Text, ASAIO, 1999.

Kay et al., "Surgical Treatment of Mitral Insufficiency", The Journal of Thoracic Surgery, 29: 618–620, 1955.

Harken et al., "The Surgical Correction of Mitral Insufficiency", The Journal of Thoracic Surgery, 28:604–627, 1954.

Bailey et al., "Closed Intracardiac Tactile Surgery", Diseases of the Chest, XXII:1–24, Jul. 1952.

Sakakibara, "A Surgical Approach to the Correction of Mitral Insufficiency", Annals of Surgery, 142:196–203, 1955.

Glenn et al., "The Surgical Treatment of Mitral Insufficiency: The Fate of A Vascularized Transchamber Intracardiac Graft", Annals of Surgery, 141:510–518, Apr. 1955.

Kay et al., "Surgical Treatment of Mitral Insufficiency", Surgery, 37:697–706, May 1955.

Bailey et al."The Surgical Correction of Mitral Insufficiency By The Use of Pericardial Grafts", The Journal of Thoracic Surgery, 28:551–603, Dec. 1954.

Harken et al., "The Surgical Correction of Mitral Insufficiency", Surgical forum, 4:4–7, 1953.

Shumacker, Jr., "Attempts to Control Mitral Regurgitation", The Evolution of Cardiac Surgery, 203–210, 1992.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," J. Card. Surg., 1996:11:99–108.

Ianuzzo et al., "On Preconditioning of Skeletal Muscle: Application to Dynamic Cardiomyoplasty," Invited Commentary, J. Card. Surg., 1996:11:109–110.

Chachques et al., "Latissimus Dorsi Dynamic Cardiomyoplasty," Ann. Thorac. Surg., 1989:47:600–604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long–Term Follow–Up (12 to 35 Weeks) After Dynamic Cardiomyoplasty," JACC, vol. 22, No. 3, Sep. 1993:758–67.

Batista et al., "Partial Left Ventriculectomy to Improve Left Ventricular Function in End–Stage Heart Disease," J. Card. Surg., 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally III Cardiac Transplant Candidates," Ann. Thorac. Surg., 1990:49:261–71.

Wampler et al., "Treatment of Cardiogenic Shock with the Hemopump Left Ventricular Assist Device," Ann. Thorac. Surg., 1991:52:506–13.

McCarthy et al., "Clinical Experience with the Novacor Ventricular Assist System," J. Thorac. Cardiovasc. Surg., 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632–636.

Bearnson et al., "Development of a Prototype Magnetically Suspended Rotor Ventricular Assist Device," ASAIO Journal, 1996, pp. 275–280.

Sakakibara et al., "A Muscle Powered Cardiac Assist Device for Right Ventricular Support: Total Assist or Partial Assist?," Trans. Am.Soc. Artif. Intern. Organs, vol. XXXVI, 1990, pp. 372–375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, "ABIOMED's Temporary Artificial Heart System Reaches 200 U.S. Medical Center Milestone," 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED" Wins NIH Grant to Develop Calcification–Resistant Plastic Heart Valve, 1 page.

Press Release dated Aug. 25, 1995, "ABIOMED Wins Research Grant from NIH to Develop Suturing Instrument for Abdominal Surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS–5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device–Blood Compatibility," *ASAIO Journal*, 1994, pp. 619–624.

Farrar et al., "A New Skeletal Muscle Linear–Pull Energy Convertor as a Power Source for Prosthetic Support Devices," *The Journal of Heart & Lung Transplantation*, vol. 11, No. 5, Sep., 1992, pp. 341–349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End--Stage Cardiomyopathy," *American Heart Journal*, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in Mitral Regurgitation," *Br. Heart J.*, vol. 49, 1983, pp. 328–333.

Pitarys II et al., "Long–Term Effects of Excision of the Mitral Apparatus on Global and Regional Ventricular Function in Humans," *JACC*, vol. 15, No. 3, Mar. 1, 1990, pp. 557–563.

Bolling et al., "Surgery for Acquired Heart Disease/Early Outcome of Mitral Valve Reconstruction in Patients with End–Stage Cardiomyopathy," *The Journal of Thoracic and Cardiovascular Surgery*, vol. 109, No. 4, Apr. 1995, pp. 676–683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138–1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso–Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404–406, Oct. 1987.

Boyd et al., "Tricuspid Annuloplasty," *The Journal of Thoracic Cardiovascular Surgery*, vol. 68, No. 3, Sep. 1974, 8 pages.

Edie, M.D. et al., "Surgical repair of single ventricle,"*The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

Lev, M.D., et al., "Single (Primitive) Ventricle," *Circulation*, vol. 39, May, 1969, pp. 577–591.

Westaby with Bosher, "Landmarks in Cardiac Surgery," 1997, pp. 198–199.

Shumacker, "Cardiac Aneurysms," *The Evolution of Cardiac Surgery*, 1992, pp. 159–165.

Feldt, M.D., "Current status of the septation procedure for univentricular heart," *The Journal of Thoracic and Cardiovascular Surgery*, vol. 82, No. 1, Jul., 1981, pp. 93–97.

Doty, M.D., "Septation of the univentricular heart," *The Journal of Thoracic and Cardiovascular Surgery*, vol. 78, No. 3, Sep., 1979, pp. 423–430.

Savage, M.D., "Repair of left ventricular aneurysm," *The Journal of Thoracic and Cardiovascular Surgery*, vol. 104, No. 3, Sep., 1992, pp. 752–762.

Cox, "Left Ventricular Aneurysms: Pathophysiologic Observations and Standard Resection," *Seminars in Thoracic and Cardiovascular Surgery*, vol. 9, No. 2, Apr., 1997, pp. 113–122.

Melvin, "Ventricular Radius Reduction Without Resection: A Computational Analysis," *ASAIO Journal*, 45:160–165, 1999.

"Heart 'jacket' could help stop heart failure progression," *Clinica*, 916, Jul. 10, 2000.

McCarthy et al., "Device Based Left Ventricular Shape Change Immediately Reduces Left Ventricular Volume and Increases Ejction Fraction in a Pacing Induced Cardiomyopathy Model in Dogs: A Pilot Study," *JACC*, Feb. 2000.

Acorn Cardiovascular, Inc. Abstracts for presentation at Nov. 2000 American Heart Association meeting, 6 pages.

Acorn Cardiovascular Summary, undated, 1 page.

"Nation's First 'Heart Jacket' Surgery to Treat Heart Failure Performed at HUP," Jun. 23, 2000, 3 pages.

Acorn Cardiovascular, Company Overview, Jun. 2000, 6 pages.

Acorn Cardiovascular, Company Overview, undated, 2 pages.

Acorn Cardiovascular, Business Plan, May 2000, 7 pages.

Acorn Cardiovascular Highlights, Abstract for presentation at American College of Cardiology, Mar. 10, 1999, 1 page.

Acorn Cardiovascular Highlights, Abstract for presentation at American Association for Thoracic Surgery, Apr. 19, 1999, 1 page.

Acorn Cardiovascular Highlights, Abstract for Poster at Heart Failure Summit V, Oct. 1, 1999, 1 page.

Acorn Cardiovascular Highlights, Abstract for presentation at American Heart Association, Nov. 9, 1999, 1 page.

* cited by examiner

METHODS AND DEVICES FOR IMPROVING MITRAL VALVE FUNCTION

BACKGROUND OF THE INVENTION

1. Field of the Invention

The present invention relates to devices and related methods for improving the function of heart valves, and more particularly to devices and related methods that passively assist in the apposition of heart valve leaflets to improve valve function of poorly functioning valves.

2. Description of the Related Art

Heart failure is a condition whereby the left ventricle becomes enlarged and dilated as a result of numerous etiologies. Initial causes of heart failure include chronic hypertension, myocardial infarction, mitral valve incompetency, and other dilated cardiomyopathies. With each of these conditions, the heart is forced to overexert itself in order to provide the cardiac output demanded from the body during its various demand states. The result is an enlarged left ventricle.

A dilated heart, and particularly a dilated left ventricle, can significantly increase the tension and/or stress in the heart wall both during diastolic filling and systolic contraction, which contributes to ongoing dilatation of the chamber. Prior treatments for heart failure include pharmacological treatments, assist devices such as pumps, and surgical treatments such as heart transplant, dynamic cardiomyoplasty, and the Batista partial left ventriculectomy. These prior treatments are described briefly in U.S. Pat. No. 5,961,440 to Schweich, Jr. et al., issued Oct. 5, 1999 and entitled "Heart Wall Tension Reduction Apparatus and Method," the complete disclosure of which is incorporated by reference herein.

A more recent concept for treating heart failure applies one or more splints onto the heart, and particulary the left ventricle, to reduce the myocardial muscular stresses encountered during pumping. Many examples of such approaches are disclosed in the if incorporated U.S. Pat. No. 5,961,440. One example includes one or more transventricular splints placed across the left ventricle. Each splint may include a tension member extending across the ventricle and anchors disposed on opposite ends of the tension member and placed on the external surface of the heart.

Mitral valve incompetency or mitral valve regurgitation is a common comorbidity of congestive heart failure. As the dilation of the ventricle proceeds, valve function may worsen. The resultant volume overload condition, in turn, increases ventricular wall stress thereby advancing the dilation process, which may further worsen valve dysfunction.

In heart failure, the size of the valve annulus (particularly the mitral valve annulus) if increases while the area of the leaflets of the valve remains constant. This may lead to an area of less coaptation of the valve leaflets, and, as a result, eventually to valve leakage. Moreover, in normal hearts, the annular size contracts during systole, aiding in valve coaptation. In heart failure, there is poor ventricular function and elevated wall stress. These effects tend to reduce annular contraction and distort annular size, often exacerbating mitral valve regurgitation. In addition, as the chamber dilates, the papillary muscles (to which the leaflets are connected via the chordae tendonae) may move radially outward and downward relative to the valve, and relative to their normal positions. During this movement of the papillary muscles, however, the various chordae lengths remain substantially constant, which limits the full closure ability of the leaflets by exerting tension prematurely on the leaflets. This condition is commonly referred to as "chordal tethering." The combination of annular changes and papillary changes results in a poorly functioning valve.

It has been observed that for at least certain placements, or orientations, of the one or more transventricular splints in humans, a pre-existing mitral valve incompetency can be exacerbated by the presence and impact of the tightened splints. The splints and the local deformation they impart may further alter the positions of the papillary muscles in such a way that the chordae do not allow as complete of a closure of the mitral valve, or that rotation of portions of the ventricular wall (to which additional chordae may be attached) may "tighten" one valve leaflet and "loosen" the other. In this manner, the leaflets may not close at the same level relative to the annulus, causing increased retrograde leakage through the valve.

Even in instances where the placement of splints does not contribute to further mitral valve leakage, it may be desirable to provide a therapy which could also correct the valve incompetency. A heart with even a small amount of regurgitation may benefit from not only the stress reducing functions of the ventricular splints as described above, but also from the elimination of the regurgitation, which will further off-load the pumping requirements of the myocardium.

While currently available methods of mitral valve repair or replacement are possible to employ in conjunction with ventricular splinting, they typically require opening the heart to gain direct access to the valve and its annulus. This type of access necessitates the use of cardiopulmonary bypass, which can introduce additional complications to the surgical procedure. Since the implantation of the splints themselves do not require the patient to be on cardiopulmonary bypass, it would be advantageous to devise a technique which could improve the mitral valve without the need for cardiopulmonary bypass. The ability to improve the mitral valve function without the need for cardiopulmonary bypass would be an advantage, both in conjunction with ventricular splinting, and also as a stand-alone therapy.

SUMMARY OF THE INVENTION

Objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. To achieve the objects and in accordance with the purpose of the invention, as embodied and broadly described herein, one aspect of the invention comprises a method for improving the function of a valve of a heart. The method includes the steps of placing an elongate member transverse a heart chamber so that each end of the elongate member extends through a wall of the heart, and placing first and second anchoring members external to the chamber. The first and second anchoring members are attached to first and second ends of the elongate member to fix the elongate member in a position across the chamber so as to reposition papillary muscles within the chamber.

According to another aspect, the invention comprises a method for improving the function of a valve of a heart. The method includes the steps of placing an elongate member transverse a heart chamber so that a first end of the elongate member extends through a wall of the heart between two papillary muscles, and a second end of the elongate member extends through a septum of the heart; placing a first anchoring member external the heart; and placing a second anchoring member inside the heart adjacent the septum. The first and second anchoring members are attached to the first and second ends of the elongate member respectively to fix the elongate member in a position across the heart chamber.

According to a further aspect, the invention comprises a method for improving the function of a valve of a heart. The method includes the steps of placing an elongate member transverse a heart chamber so that each end of the elongate member extends through a wall of the heart; and placing first and second anchoring members external the chamber. The first and second anchoring members are attached to the ends of the elongate member to fix the elongate member in a position across the chamber. The position is superior to the papillary muscles and proximate and substantially across the valve.

According to an even further aspect, the invention comprises a splint for improving the function of a valve of a heart. The splint includes an elongate member configured to be positioned transverse a heart chamber so that each end of the elongate member extends through a wall of the heart, and first and second anchoring members configured to be positioned external the chamber and attached to the ends of the elongate member to fix the elongate member in a position across the chamber. The first anchoring member includes a first portion configured to contact a first region of the heart proximate the valve to change a shape of the valve. Preferably, the first portion will contact a first region of the heart proximate the valve annulus to change the shape of the valve annulus.

According to another aspect, the invention comprises a splint for improving the function of a valve of a heart. The splint includes an elongate member configured to be positioned transverse a heart chamber so that each end of the elongate member extends through a wall of the heart, first and second anchoring members configured to be positioned external the chamber and attached to the ends of the elongate member to fix the elongate member in a position across the chamber, a third anchoring member connected to at least one of the first and second anchoring members by a connection member. The third anchoring member is configured to contact a region of the heart proximate the valve to change a shape of the valve.

According to a further aspect, the invention comprises a device for improving the function of a valve of a heart. The device includes a first splint having a first elongate member configured to be positioned transverse a heart chamber so that each end of the elongate member extends through a wall of the heart, and a first anchoring member configured to be positioned external the chamber and attached to a first end of the first elongate member. The device further includes a second splint having a second elongate member configured to be positioned transverse a heart chamber so that each end of the second elongate member extends through a wall of the heart, and a second anchoring member configured to be positioned external the chamber and attached to a first end of the second elongate member. The device also includes a connecting mechanism configured to be connected to the second ends of each of the first and second elongate members external the chamber and press the wall of the heart chamber to change a shape of the valve.

Yet a further aspect of the invention includes a method for improving cardiac function, comprising placing a first member relative to a heart chamber to alter the cross-sectional shape of the chamber and placing a second member relative to a valve of the heart chamber to assist in apposition of leaflets of the valve.

According to an even further aspect, the invention includes a method of improving the function of a valve of a heart comprising applying a force to an exterior surface of a wall surrounding a chamber of the heart substantially at a location of the valve to alter a shape of the valve.

Yet a further aspect of the invention includes a method for improving the function of a valve of a heart comprising placing a device relative to the heart to alter a shape of the valve and adjusting the device relative to the heart based on data obtained during the adjusting from real-time monitoring of valve function.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 3b is an external view of a human heart showing the orientation of the mitral valve splint and series of transventricular splints of FIG. 3a;

DESCRIPTION OF THE PREFERRED EMBODIMENTS

Figure 1:
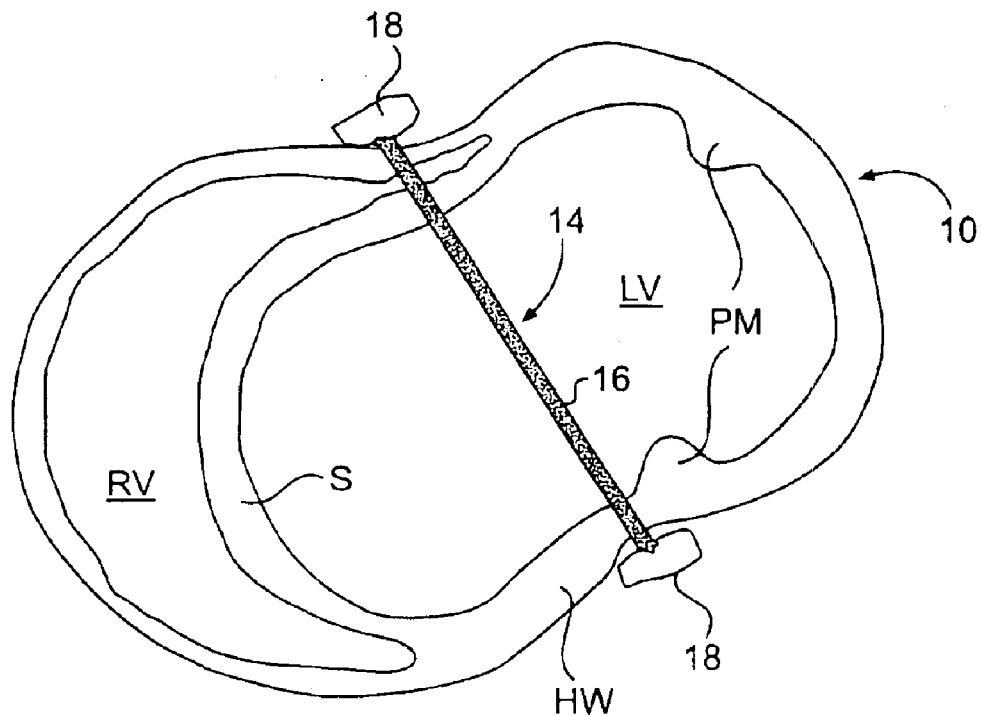
FIG. 1 is a transverse cross section of the left and right ventricles of a human heart showing the placement of splints according to an orientation for lessening myocardial muscular stresses.

The various aspects of the invention to be discussed herein generally pertain to devices and methods for treating heart conditions, including, for example, dilatation, valve incompetencies, including mitral valve leakage, and other similar heart failure conditions. Each device of the present invention preferably operates passively in that, once placed in the heart, it does not require an active stimulus, either mechanical, electrical, or otherwise, to function. Implanting one or more of the devices of the present invention operates to assist in the apposition of heart valve leaflets to improve valve function. In addition, these devices may either be placed in conjunction with other devices that, or may themselves function to, alter the shape or geometry of the heart, locally and/or globally, and thereby further increase the heart's efficiency. That is, the heart experiences an increased pumping efficiency through an alteration in its shape or geometry and concomitant reduction in stress on the heart walls, and through an improvement in valve function.

The inventive devices and related methods offer numerous advantages over the existing treatments for various heart conditions, including valve incompetencies. The devices are relatively easy to manufacture and use, and the surgical techniques and tools for implanting the devices of the present invention do not require the invasive procedures of current surgical techniques. For instance, the surgical technique does not require removing portions of the heart tissue, nor does it necessarily require opening the heart chamber or stopping the heart during operation. For these reasons, the surgical techniques for implanting the devices of the present invention also are less risky to the patient than other techniques. The less invasive nature of the surgical techniques and tools of the present invention may also allow for earlier intervention in patients with heart failure and/or valve incompetencies.

The disclosed inventive devices and related methods involve geometric reshaping of the heart and treating valve incompetencies. In certain aspects of the inventive devices and related methods, substantially the entire chamber geometry is altered to return the heart to a more normal state of stress. Models of this geometric reshaping, which includes a reduction in radius of curvature of the chamber walls, can be found in U.S. Pat. No. 5,961,440 incorporated above. Prior to reshaping the chamber geometry, the heart walls experience high stress due to a combination of both the relatively large increased diameter of the chamber and the thinning of the chamber wall. Filling pressures and systolic pressures are typically high as well, further increasing wall stress. Geometric reshaping according to the present invention reduces the stress in the walls of the heart chamber to increase the heart's pumping efficiency, as well as to stop further dilatation of the heart.

Although many of the methods and devices are discussed below in connection with their use in the left ventricle and for the mitral valve of the heart, these methods and devices may be used in other chambers and for other valves of the heart for similar purposes. One of ordinary skill in the art would understand that the use of the devices and methods described herein also could be employed in other chambers and for other valves of the heart. The left ventricle and the mitral valve have been selected for illustrative purposes because a large number of the disorders that the present invention treats occur in the left ventricle and in connection with the mitral valve. Furthermore, the devices disclosed herein for improving valve function can be "stand-alone" devices, that is, they do not necessarily have to be used in conjunction with devices for changing the shape of a heart chamber or otherwise reducing heart wall stress. It also is contemplated that a device for improving valve function may be placed relative to the heart without altering the shape of the chamber, and only altering the shape of the valve itself.

Reference will now be made in detail to the present preferred embodiments of the invention, examples of which are illustrated in the accompanying drawings. Wherever possible, the same reference numbers will be used throughout the drawings to refer to the same or like parts.

A currently preferred orientation of transventricular splints for lessening myocardial muscular stresses is shown in FIG. 1, which shows the short-axis left ventricular cross-section from an anterior perspective. Examples of particular transventricular splints that are especially suitable for this application include those shown and described in copending U.S. patent application Ser. No. 09/532,049 to Vidlund et al., filed Mar. 21, 2000, entitled "A Splint Assembly for Improving Cardiac Function in Hearts, and Method for Implanting the Splint Assembly," and commonly assigned to the assignee of the present invention. The complete discosure of that application is incorporated by reference herein. That application will be referred to as "the '049 application" in the remainder of this disclosure.

In the preferred orienation shown in FIG. 1, three splints are placed in a coplanar fashion, along the long axis of the ventricle, bisecting the left ventricle LV of the heart 10. FIG. 1 is a cross-section (short axis) view looking from the superior side of the heart. The superior-most splint 14 is placed at approximately the level of the heads of the papillary muscles PM and below the level of leaflet coaptation, and the additional two splints (not shown in FIG. 1) are placed inferiorly toward the apex. The preferred orientation shown in FIG. 1 both bisects the left ventricle LV and avoids key structures such as coronary vessels and the like. The splints according to this orientation also extend through the septum S near its edge and enter a small portion of the right ventricle RV.

Each splint includes a tension member 16 and an anchor assembly 18 at each end of the tension member 16. Presently preferred embodiments of tension members 16, anchor assemblies 18, and their connection to one another are disclosed in the '049 application incorporated by reference above. As shown in FIG. 1, tension member 16 extends through heart wall HW, across the left ventricle LV, and through the septum S and a portion of the right ventricle RV. Anchor assemblies 18 are placed adjacent the external surface of the heart wall HW, and therefore, in the exemplary embodiment shown, external to the heart 10 and contacting cardiac structure other than structure of the valve.

Figure 2A:
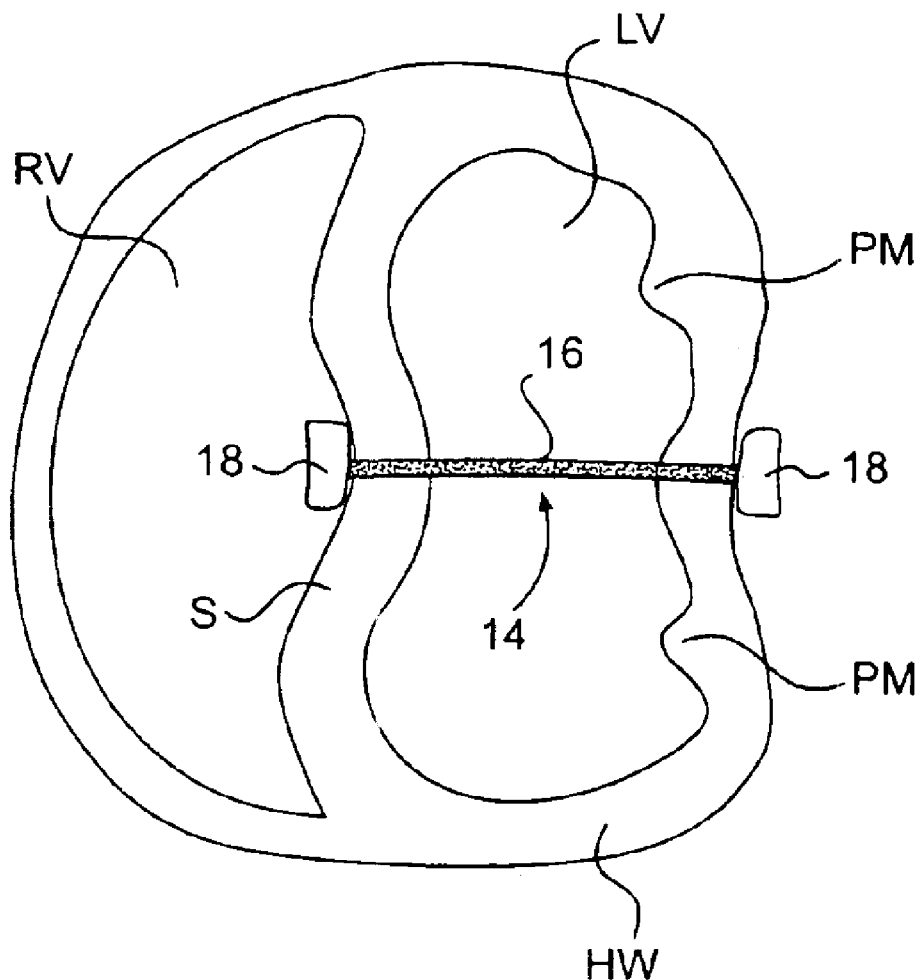
FIG. 2a is a transverse cross section of the left and right ventricles of a human heart showing the orientation of splints according to an embodiment of the present invention for lessening myocardial muscular stresses and assisting in apposition of valve leaflets.

As mentioned above, human implantations of splints, including in an orientation shown in FIG. 1, may exacerbate any pre-existing mitral valve incompetency, including mitral valve regurgitation (MVR), or at the least, may not improve any pre-existing MVR. FIG. 2a shows an orientation of splints 14 according to an embodiment of the present invention which may assist in both offloading myocardial wall stress and in aiding the apposition of valve leaflets. According to this orientation, each tension member 16 of splint 14 extends through the heart wall HW at a position approximately midway between the antero lateral papillary muscle PM and the postenio medial papillary muscle PM, extends transverse the left ventricle LV, and extends through the septum S at approximately its midpoint. A first anchor assembly 18 is placed external the heart 10 adjacent the heart wall HW and a second anchor assembly is placed inside the right ventricle RV adjacent septum S. FIG. 2a shows the superior-most splint 14 of preferably three splints, with the other two splints placed inferiorly towards the apex. More or less than three splints may be used. The splints in this orientation are generally parallel to one another and substantially perpendicular to the long axis of the left ventricle.

The orientation of splints 14 shown in FIG. 2a helps to "pull" both of the papillary muscles PM toward the center of the left ventricle LV and reposition those muscles closer to their normal physiological position relative to the mitral valve annulus during the complete cardiac cycle. During the course of heart failure dilation, the papillary muscles PM are moved laterally away from their normal position, which causes the chordae connected to both valve leaflets to become excessively taut. This in turn inhibits the leaflets from fully closing against each other. By bringing the papillary muscles PM closer to the center of the ventricle LV, the chordae are slackened enough to allow the leaflets to appose, thereby improving on mitral valve function. Additionally, although the splints 14 in this approach are preferably positioned at and below the level of the tops of the papillary muscles PM, the shape change deformation at the superior-most splint 14 would extend in a region further superior, and potentially include the annulus itself. To the extent that the annulus in the region of the posterior leaflet is deformed, this would further benefit the valve function by reducing the cross-sectional area of the annul us and positioning the posterior leaflet and its attachment zone closer to the anterior annulus. This, in turn, will cause the leaflets to more fully appose, minimizing MVR.

Various methods may be employed to implant the splints 14 in the orientation shown in FIG. 2a. One particularly advantageous method is an endosvasular delivery technique shown and described in co-pending U.S. patent application Ser. No. 09/679,550 to Robert M. Vidlund et al., entitled "Endovascular Splinting Devices and Methods," filed on the same day as this application and commonly assigned to the assignee of this application, the entire disclosure of which is incorporated by reference herein. Splints 14 also may be positioned in the orientation shown in FIG. 2a by other surgical techniques, such as those described in the '049 application incorporated by reference above. For example, to gain access to the ventricular septum S, a small incision can be placed within the right ventricular wall to allow for positioning tension member 16 and the anchor assembly 18 within the right ventricle RV. The methods of implantation shown and described in the applications referred to above may be used in connection with any of the embodiments shown and described herein.

Figure 2B:
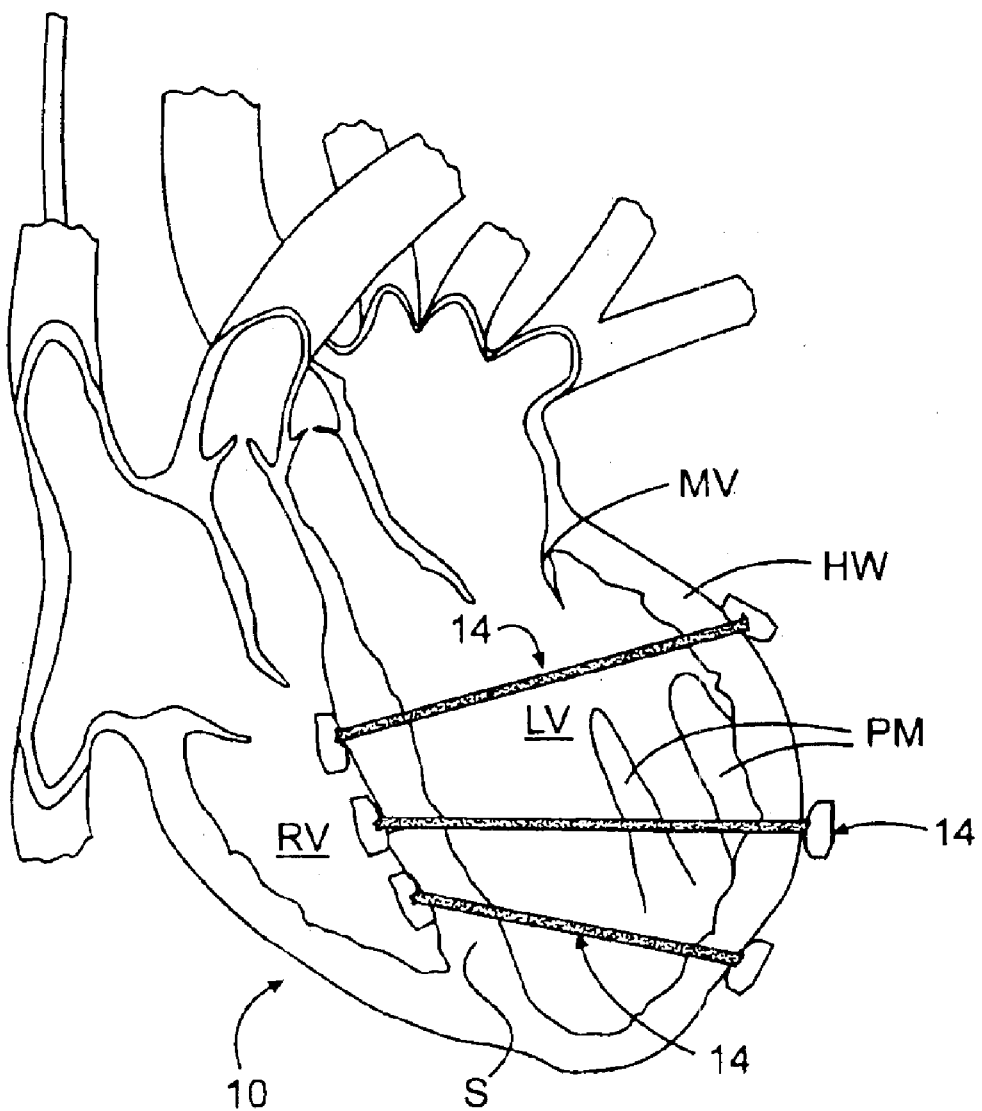
FIG. 2b is a vertical cross section of the left and right ventricles of a human heart showing another orientation of ventricular shape change splints according to an embodiment of the present invention for lessening myocardial muscular stresses and assisting in apposition of valve leaflets.

FIG. 2b shows another orientation of splints 14 according to an embodiment of the present invention which may assist in the offloading of myocardial wall stress and in the apposition of valve leaflets. According to this orientation, at least one splint 14 is angled with respect to the long axis of the left ventricle LV, in contrast to orienting the at least one splint 14 perpendicular to the axis of the left ventricle LV. In the embodiment shown in FIG. 2b, the lower two splints 14 are angled relative to the ventricular axis and relative to the superior-most splint 14, which is approximately perpendicular to the ventricular axis. In this example, all three splints 14 are coplanar, as is preferred for optimizing the ventricular shape change. While FIG. 2b illustrates the ventricular splints having an anchor pad disposed on the septum, it is contemplated that the benefits of angling one or more splints relative to the long axis of the ventricle could be achieved at other cross-sectional orientations including, for example, the orientation shown in FIG. 1, in which an anchor pad is located on an exterior wall of the heart as opposed to the septum wall.

Because the lower two splints 14 are positioned at an angle, they tend to "lift" one or both papillary muscles PM as they impart shape change to the left ventricle LV. By lifting the papillary muscle(s) PM, some slack may be provided to the chordae connected to the valve leaflets to permit improved apposition of the leaflets of mitral valve MV. It is contemplated that more or less splints than the lower two splints may be angled (other than perpendicularly) relative to the ventricular axis to achieve the benefits to MVR, and that each splint may have a different angle relative to that axis. For example, all three splints could be angled, or only one splint could be angled. The number of splints to be angled, and the degree of such angles, would be chosen to optimize the improvement in MVR and would depend on factors such as the particular anatomy of a heart. The splint positioning can be iteratively changed and the impact on MVR, and mitral valve function in general, can be monitored using appropriate "real-time" imaging techniques and equipment, such as, for example, ultrasound and other suitable mechanisms. The ventricular splints 14 shown in FIG. 2b may be oriented in any suitable cross sectional position, including the positions shown in FIG. 1 or 2a. The benefits to MVR of angularly positioning one or more of the ventricular splints 14 relative to the ventricular axis, as shown in FIG. 2b, may be achieved independent of the particular cross sectional position of the splints 14.

According to an embodiment of the present invention, a method of improving mitral valve function, while maintaining the positions and orientations of the ventricular splints shown in FIG. 1, includes the use of an additional splint. This additional splint, referred to herein as a mitral valve splint or MV splint, preferably has the same construction as the other splints and may be implanted using the similar delivery techniques. The primary function of the MV splint is to impart a shape change to the mitral valve annulus, adjacent the left ventricular wall, as well as reposition the papillary muscles PM.

Figure 3A:
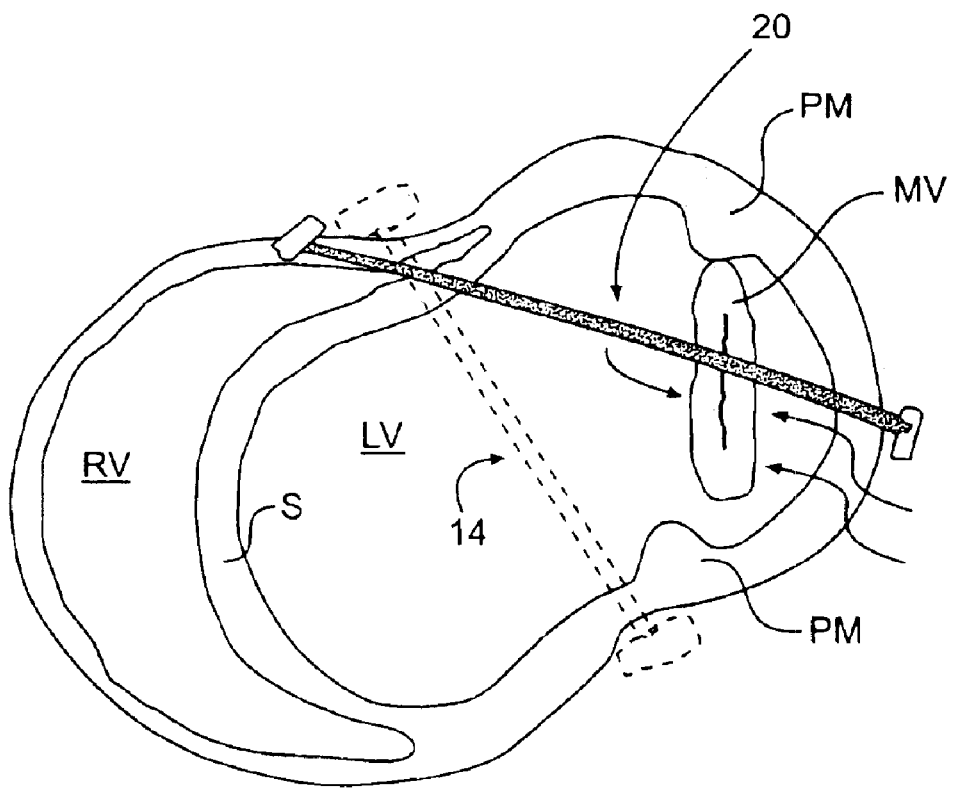
FIG. 3a is a transverse cross section of the left and right ventricles of a human heart showing an orientation of a mitral valve splint used in combination with a series of transventricular splints according to an embodiment of the present invention for lessening myocardial muscular stresses and assisting in apposition of valve leaflets.
Figure 3B:
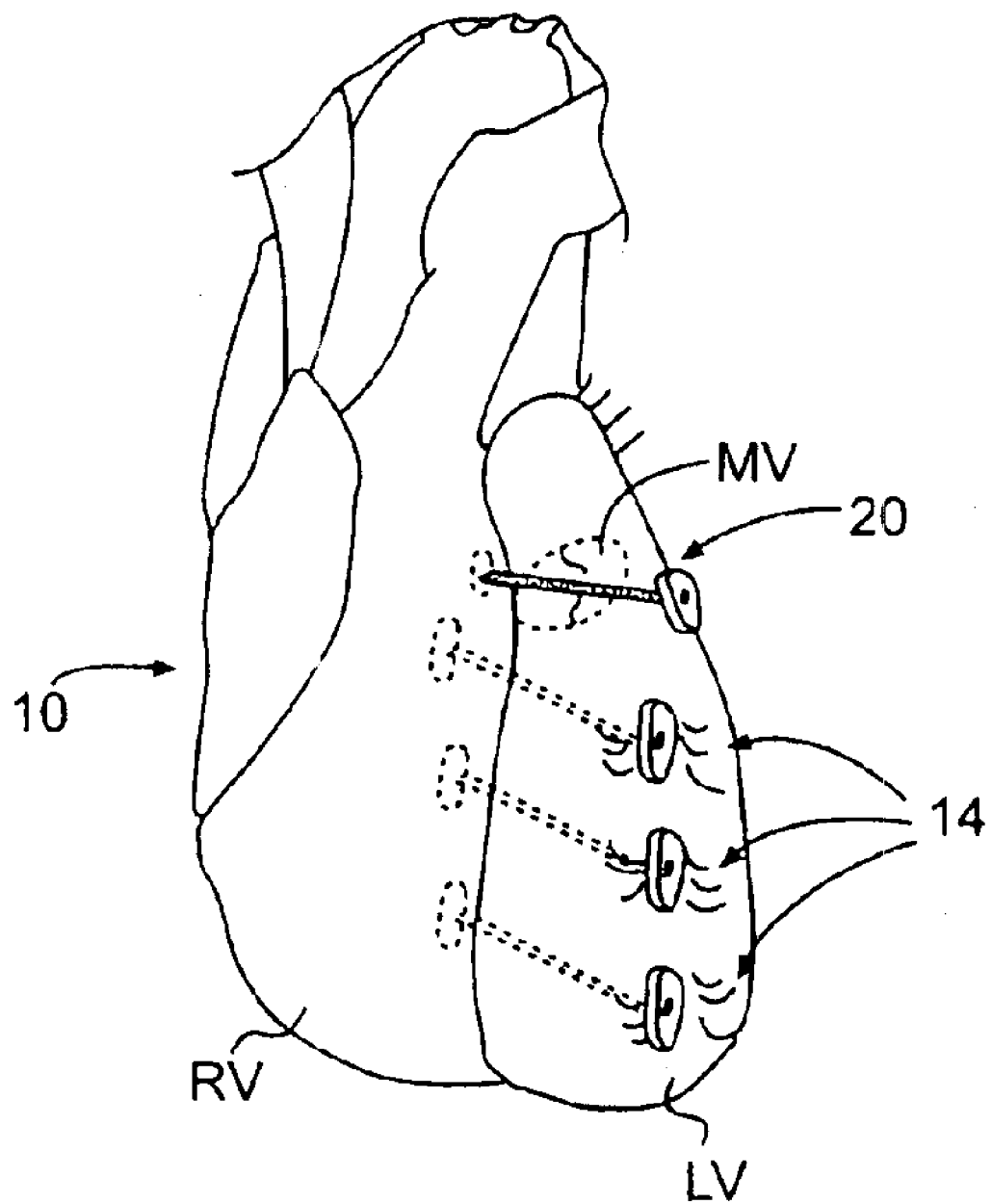

FIGS. 3a and 3b show an MV splint according to an embodiment of the present invention. FIGS. 3a and 3b show the three ventricular splints 14 in the positions and orientations shown and described in connection with FIG. 1 (the dashed lines in FIGS. 3a, 3b) and show an exemplary orientation of an MV splint 20. It should be noted that in FIGS. 3a and 3b the shape change to the left ventricle caused by the transventricular splints 14 is not illustrated. MV splint 20 is positioned superior to the papillary muscles PM and oriented primarily across the mitral valve MV and on or below the mitral valve annulus while avoiding key vascular structures. In this orientation, MV splint 20 is "out of plane" with the other ventricular splints 14, as the overall function of MV splint 20 is to improve and optimize the mitral valve function. In the example shown in FIGS. 3a and 3b, the MV splint extends transverse the left ventricle LV, through the septum S, through the right ventricle RV, and once again through the heart wall. As shown in FIGS. 3a and 3b, and as described with respect to the transventricular splints 14 of FIG. 1, the anchor assemblies of the MV splint may be placed adjacent an external surface of the heart wall HW and may be external to the heart and contacting cardiac structure other than structure of the heart valve, for example.

The MV splint 20 improves mitral valve function through a combination of effects. First, the shape of the annulus is directly altered, preferably during the entire cardiac cycle, thereby reducing the annular cross sectional area and bringing the posterior leaflet in closer apposition to the anterior leaflet. Second, the position and rotational configuration of the papillary muscles PM and surrounding areas of the left ventricle LV are further altered by the tightening of the MV splint 20. This places the chordae in a more favorable state of tension, allowing the leaflets to more fully appose each other. Third, since the annulus of the valve is muscular and actively contracts during systole, changing the shape of the annulus will also reduce the radius of curvature of at least portions of the annulus, just as the shape change induced by the ventricular splints reduces the radius of at least significant portions of the ventricle. This shape change and radius reduction of the annulus causes off-loading of some of the wall stress on the annulus. This, in turn, assists the annulus's ability to contract to a smaller size, thereby facilitating full closure of the mitral valve MV during systole.

The position of the MV splint 20 shown in FIGS. 3a and 3b is exemplary. The ventricular splints 14 preferably are positioned prior to positioning MV splint 20, through the use of, for example, both angiographic and ultrasonic visualization tools. This It positioning technique, described in the '049 application incorporated above, achieves optimal positioning of splints 14 to bisect the left ventricle LV and avoid key anatomic structures. After positioning the ventricular splints 14, a device such as the probe/marking device shown and described in the '049 application may be used to repeatedly probe and deform possible areas near the mitral valve to find the optimal position for the MV splint 20. By utilizing, for example, standard "real-time" ultrasonic imaging techniques, the direct impact of the probing on MVR can be assessed, and pre-existing MVR or MVR exacerbated by placement of the ventricular splints 14 can be corrected. Once the optimal position for an MV splint 20 is determined and marked, the MV splint 20 is implanted and positioned by any of the delivery techniques referred to above, including the endovascular delivery technique or the more direct surgical approaches. The use of the MV splint 20 allows for the optimal placement of the ventricular splints 14, which reduce heart wall stress, independent from the optimal subsequent positioning of the MV splint 20, which improves mitral valve function. During implantation, the splint can be adjusted (either in position or in tightness or both) to optimize improvement to valve function, as determined by observation of the valve using real-time imaging techniques.

Figure 3C:
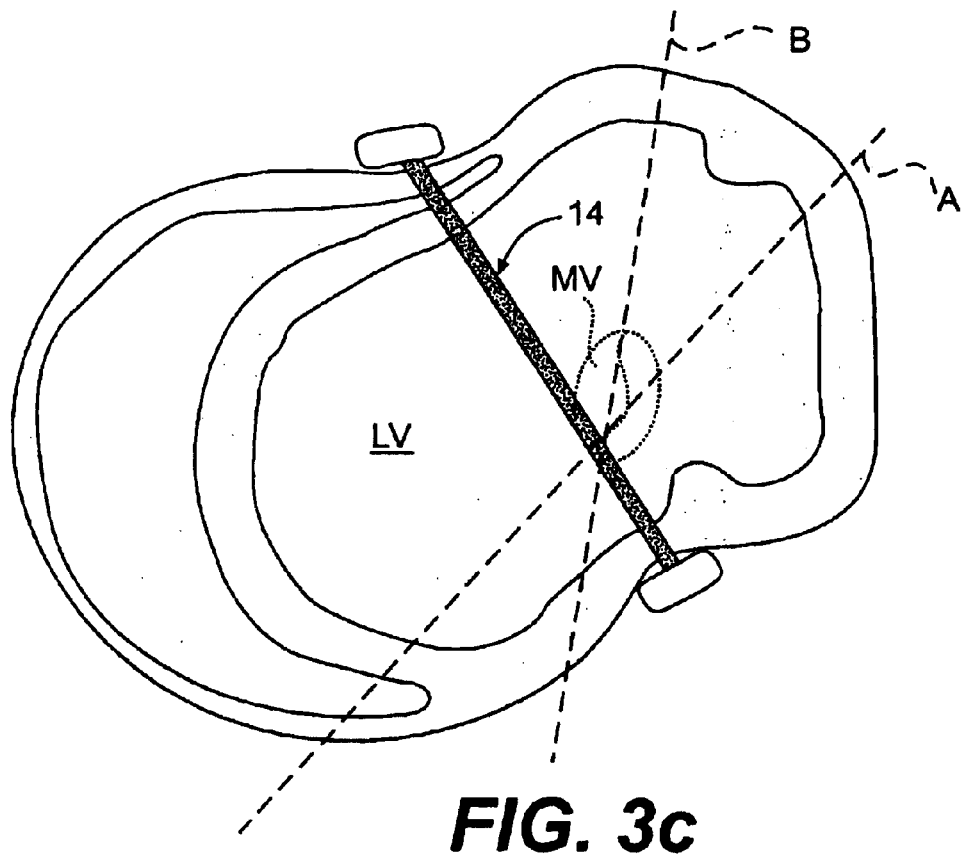
FIG. 3c is a transverse cross section of the left and right ventricle of a human heart showing a various orientations for a mitral valve splint used in combination with a series of transventricular splints according to an embodiment of the present invention.

It is anticipated that the optimal position of the MV splint 20 could be at virtually any orientation relative to the valve leaflets, depending on the heart failure and mitral valve regurgitation associated with the particular heart at issue. For example, in some hearts, the position shown and described in connection with FIGS. 3a and 3b may yield the most improvement of MVR, whereas in other hearts, alternative positions such as shown in FIG. 3c may yield the most improved results. Note that in FIG. 3c, the transventricular splint is shown positioned between the papillary muscles, which may be another preferred orientation for certain hearts. Alternative "A" places MV splint to cause shape change between the papillary muscles Alternative "B" for MV splint positioning would be in a line more parallel to the valve leaflet edges, as shown in FIG. 3d. Other placements of the MV splint, as well as the position of the transventricular splints, relative to the heart also are contemplated and could be selected based on the condition of the heart and the mitral valve.

Figure 4A:
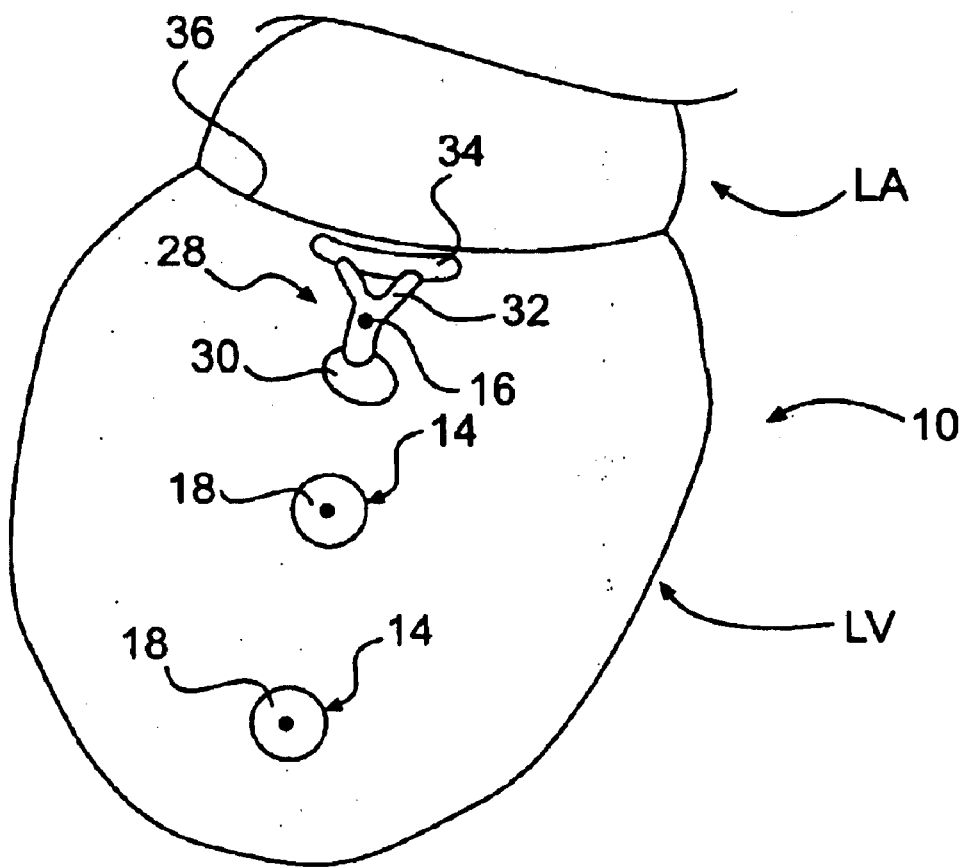
FIG. 4a is an external view of a human heart showing a series of transventricular splints, with the superior-most splint having an anchor structure according to an embodiment of the present invention that assists in apposition of valve leaflets.

According to another embodiment of the present invention, an alternative anchor assembly for the ventricular splints 14 may be provided to aid in mitral valve function. In the embodiment shown in FIG. 4a, the superior-most splint 14 includes an anchor assembly 28 configured for connection to the "free wall" end of that splint 14, i.e., at the exterior wall of the left ventricle. Anchor assembly 28 includes a lower portion in the form of, for example, a lower pad portion 30 which contacts the external surface of the left ventricle wall somewhat below the level of the tension member 16. In a preferred embodiment, the lower pad portion 30 resembles the shape, size, and construction of the anchor pads described in the '049 application incorporated above. Anchor assembly 28 further includes an upper portion in the form of, for example, an upper pad portion 34 which contacts a superior region of the left ventricle wall near the mitral valve annulus. Tension member 16 connects to a spanning structure 32 that, in one embodiment, is preferably integrally fabricated with the lower and upper pad portions 30 and 34, and connects portions 30 and 34. Suitable materials for anchor assembly may include, but are not limited to, those described in the '049 application. At least the lower and upper pad portions 30 and 34 preferably include a covering or a coating of a material, such as, for example, a woven polyester fabric, to encourage tissue in-growth. The spanning structure 32 also may be made of, or include a covering or coating made of, a material to encourage tissue in-growth In the exemplary, preferred embodiment shown in FIG. 4a, the lower pad portion 30 has a circular shape and the upper pad portion 34 has an oblong shape. The oblong shape of the upper pad portion 34 has the advantage of inducing relatively extensive shape change along the periphery of the valve annulus, preferably during the entire cardiac cycle. Therefore, in an embodiment, the length and shape of the upper pad portion may extend a significant distance around the valve annulus. For example, the upper pad portion 34 may extend from about 1 cm in length to about 10 cm in length, depending on the desired shape change of the valve annulus. The width of the upper pad portion 34, however, is preferably relatively narrow, so as to concentrate its shape change impact to the region near the valve annulus.

The upper pad portion 34 may be positioned near, but below, the valve annulus. In other embodiments of the present invention, the upper pad portion may be positioned directly on the exterior surface of the annulus or somewhat above the annulus to contact the left atrium wall. The position of the upper pad portion preferably avoids direct compressive contact with important vascular structure near or on the exterior surface of the heart. Significant coronary vasculature often lies on or near the atrio-ventricular groove 36, which corresponds with the posterior annular region of the mitral valve. For this reason, it may be desirable to position the upper pad portion onto the left atrial surface.

Anchor assembly 28 permits selection of a position that causes valve annulus shape change relatively independent from the positioning of the ventricular splints that cause ventricular shape change. The incorporation of an anchor assembly 28 is most suitable for instances where the desired shape change for the mitral valve is relatively co-planar with the main ventricular shape change splints. In addition, anchor assembly 28 provides for annulus shape change without the need for an additional MV splint, such as that shown in FIGS. 3a and 3b.

Figure 4B:
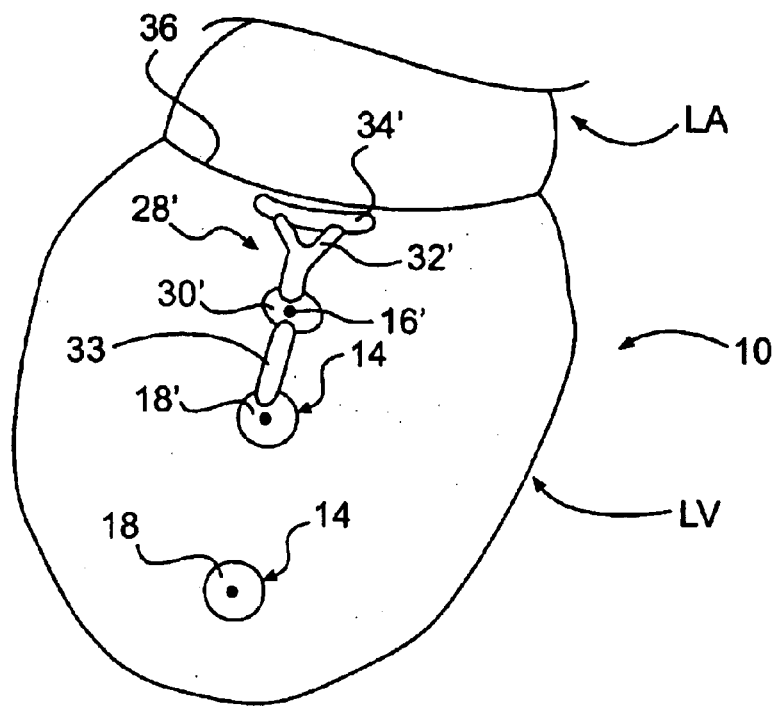
FIG. 4b is an external view of a human heart showing a series of transventricular splints, with the superior most splint having an anchor structure and a connection mechanism between the superior most and middle anchors according to yet another embodiment of the present invention that assists in apposition of valve leaflets.

An alternative embodiment of a splint with a mitral valve anchor assembly according to the invention is illustrated in FIG. 4b. In the embodiment of anchor assembly 28, shown in FIG. 4a, the tension member 16 was connected to the spanning structure 32 approximately in the middle of the spanning structure 3, yielding a relatively stable structure that remains substantially parallel to the exterior surface of the heart. However, the embodiment of the anchor assembly 28' shown in FIG. 4b places the ventricular shape change caused by the lower pad portion 30' below the end of the tension member 16'. The anchor assembly 28' illustrated in FIG. 4b is similar to the anchor assembly 28 of FIG. 4a, except that the tension member 16' is anchored within the lower pad portion 30'. In order to provide mechanical balance to the anchor assembly, and to give leverage to the upper pad portion 34' such that it can properly alter the region of the valve annulus, a second spanning structure 33 is provided to mechanically connect the anchor assembly 28' to an anchor pad 14 of the splint disposed below the superior-most splint. This second spanning structure 33 also may be integrally formed with the anchor assembly 28' and, in turn, with the anchor pad 14. Alternatively, the second spanning structure 33 can be a separate component connecting anchor assembly 28' and anchor pad 14' once they are positioned with respect to the heart. This could be done, for example, by mechanical fastening, such as with screws or the like.

Figure 4C:
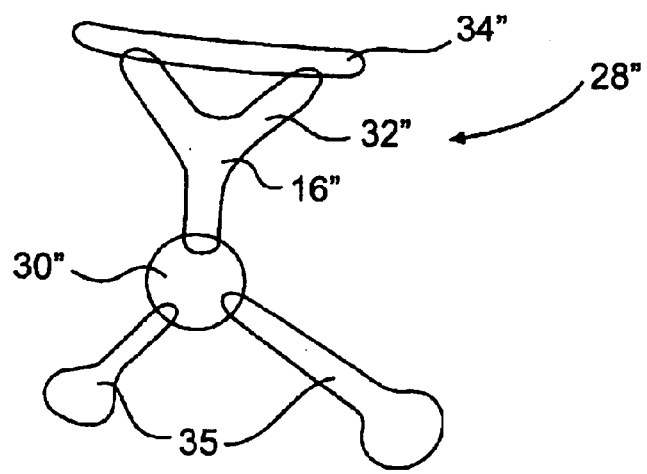
FIG. 4c is a perspective view of an anchor assembly for a transventricular splint according to yet another embodiment of the present invention that assists in apposition of valve leaflets and repositioning of papillary muscles.

A further alternative anchor assembly 28" is shown in FIG. 4c. This anchor assembly 28" is similar to the anchor assembly 28 shown in FIG. 4a, except that anchor assembly 28" also includes one or more additional papillary pad portions 35 connected to lower pad portion 30" at a location substantially opposite to spanning structure 32" The papillary pad portion or portions 35 serve to provide one or more additional sites of deformation of the ventricular wall, preferably to further reposition one or both papillary muscles to aid in appoistion of the valve leaflets. The papillary pad portions 35 may be formed integrally with the anchor assembly 28" or may be separate and connected thereto via suitable connection mechanisms.

In certain cases, the optimal orientation of shape change for improving the mitral valve function may be significantly offset from the position and orientation of transventricular splints 14. It is therefore desirable to have an approach to cause mitral valve shape change at positions away from the transventricular splints 14, and even more desirably, without the addition of another splint structure traversing the ventricle.

Figure 5A:
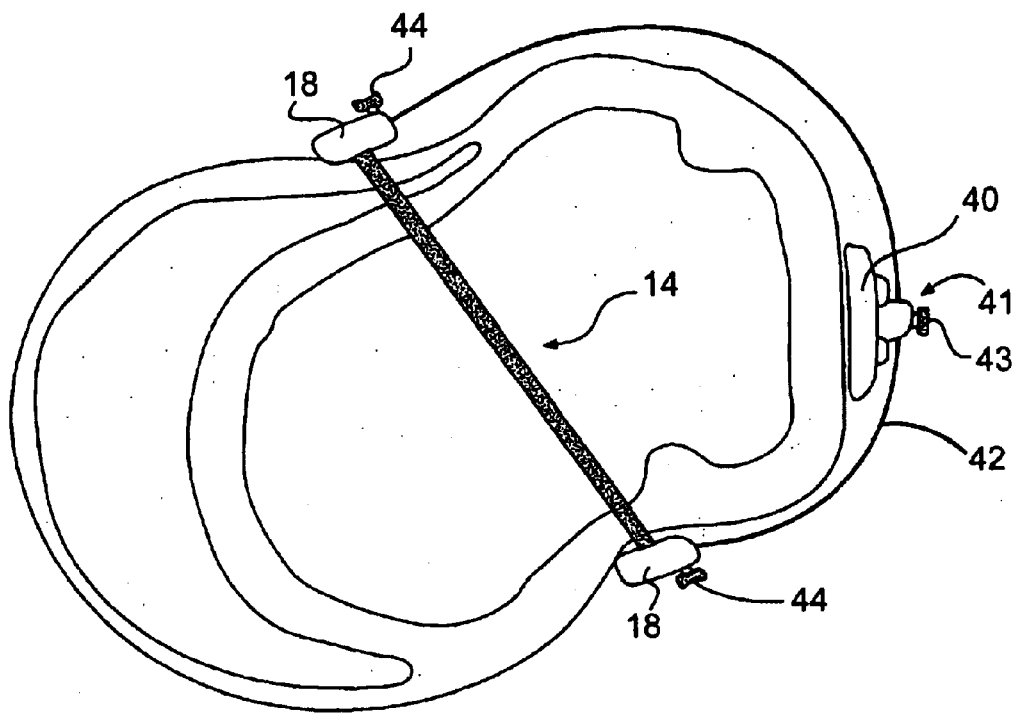
FIG. 5a is a transverse cross section of the left and right ventricles of a human heart showing the placement of splints according to an orientation for lessening myocardial muscular stresses with an accessory anchor assembly according to an embodiment of the present invention to assist in apposition of valve leaflets.

FIG. 5a shows such an approach according to an embodiment of the present invention. FIG. 5a shows an accessory anchor pad structure 40 attached to a connection member, shown as a runner 42. Runner 42 connects at its ends to both anchor pads 18 of preferably the superior-most splint assembly 14. As an alternative, runner 42 may connect to one anchor pad 18 and extend between that anchor pad 18 and structure 40. The accessory pad structure 40 is positioned at the location on the heart wall that yields the greatest improvement in MVR, as determined with repeated probing and deforming at the exterior of the heart proximate the mitral valve annulus, as described above in connection with positioning the MV splint 20 in FIGS. 3a and 3b.

Since runner 42 preferably connects to the two anchor pads 18 of the upper-most splint assembly 14, runner 42 generally runs at approximately the same level on the heart wall as those anchor pads 18. In one embodiment, accessory anchor pad structure 40 may be of the same shape and material as the anchor pads 18. While this embodiment may result in significantly improved MVR in some instances, in another embodiment, accessory pad 40 may take a form, including shape and material, similar to the anchor assemblies 28, 28', 28" shown in FIGS. 4a–4c. This latter configuration permits positioning accessory pad 40 at a position higher than the level of the anchor pads 18 of the superior-most transventricular splint, resulting in even greater shape change to the mitral valve annulus. Also according to this latter configuration, the preferred construction of accessory pad 40 would include, in addition to characteristics of anchor assembly 28, 28', 28", shown in FIGS. 4a–4c, a connecting mechanism 41 which would allow for adjustable positioning and securing of the accessory pad 41 to runner 42. For example, a locking screw 43 may be used to secure runner 42 to pad 41. Other mechanisms suitable for securing the pad 41 to the runner 42 and permitting adjustment of the pad position along the runner are within the scope of the present invention. Runner 42 preferably includes a wire-like, or braid-like, structure which secures to each of the splint anchor pads 18 also through any suitable means, such as, for example, a locking screw mechanism 44, a pinning connection for a braid-like runner, or the like.

Figure 5B:
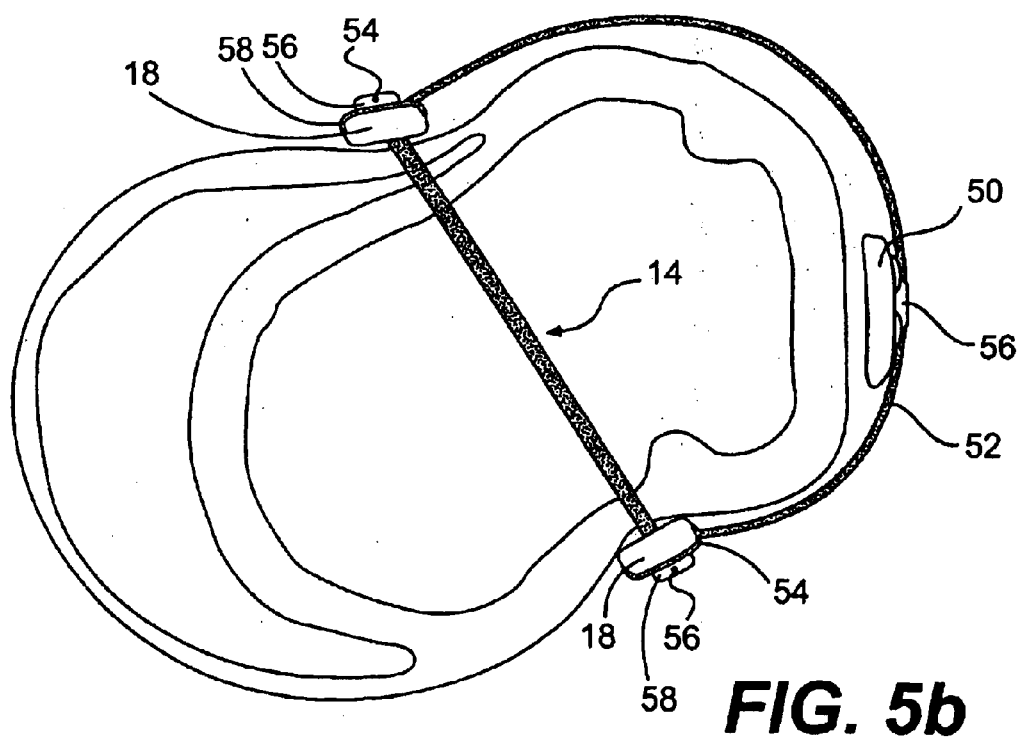
FIG. 5b is a transverse cross section of the left and right ventricles of a human heart showing the placement of splints according to an orientation for lessening myocardial muscular stresses with an accessory anchor assembly according to another embodiment of the present invention to assist in apposition of valve leaflets.

FIG. 5b shows an alternative embodiment for connecting an accessory anchor pad assembly 50 to a runner 52 and for connecting runner 52 to anchor pads 18. Each end of runner 52 connects to a connection mechanism in the form of a cap 54. Each cap 54 locks in place over a pad 18. At least one of the caps 54 includes an adjustable locking mechanism for adjusting the length of the runner 52 between the caps 54, and also thereby adjusting the position of the accessory pad 50 on the heart wall, and locking the runner 52 to cap 54.

In one embodiment, runner 52 is a braid formed of a high strength polymer, such as that used in the tension members described in the '049 application incorporated above. A suitable connection mechanism includes the use of one or more pins 56 placed through the braided runner 52 and connected to cap 54 through a flange 58, for example, situated on the cap 54. This pinning connection mechanism may be similar to the connection used for the braided tension members and anchor pads shown and described in the '049 application. The same connection mechanism may be used to connect accessory pad 50 to braided runner 52. In an alternative embodiment according to the present invention, the braided runner 52 may more directly connect to anchor pads 18, without the use of caps 54, by, for example, a pinning securement mechanism incorporated into the superior splint pads themselves. In another contemplated embodiment, the external anchor pad assembly 50, including the runner 52 and anchor pads 18, can be used without the transventricular splint to improve valve function by causing a shape change to the valve annulus without an overall shape change to the left ventricle.

As mentioned above, a mechanism that may exacerbate MVR is the relative rotation of the papillary muscles PM and the adjacent left ventricular wall as the transventricular splints 14 are tightened into position. This relative rotation results in slack in some chordae and tightening in other chordae, which may "pull" one valve leaflet (or portion of the leaflet) while "loosening" the other valve leaflet (or portion of the leaflet).

Figure 6:
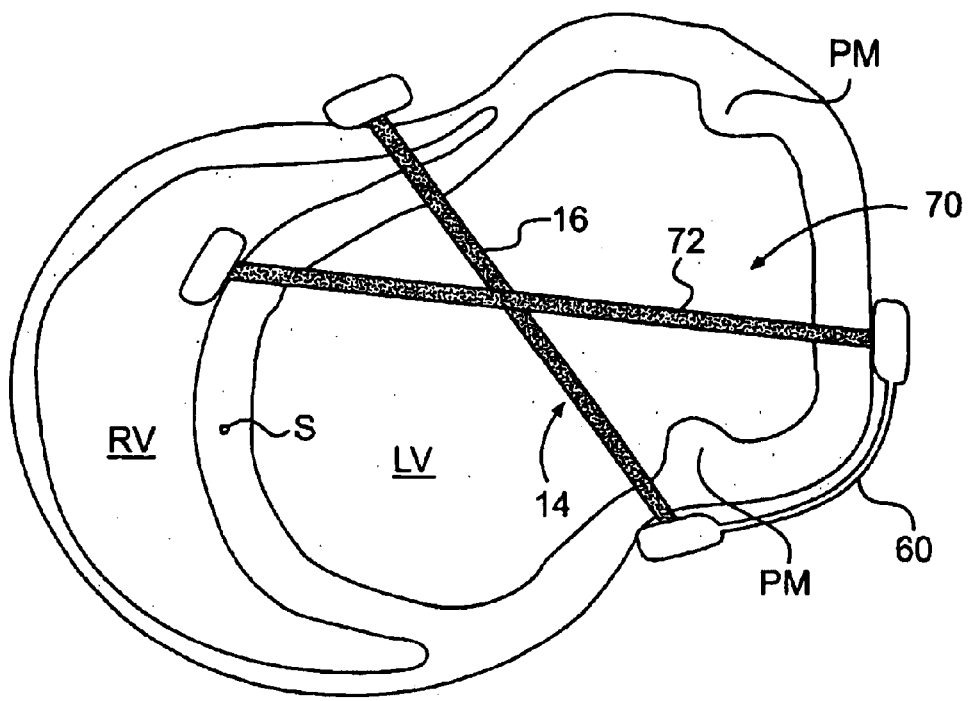
FIG. 6 is a transverse cross section of the left and right ventricles of a human heart showing an orientation of a mitral valve splint used in combination with a series of transventricular splints, with an interconnecting mechanism according to an embodiment of the present invention for lessening myocardial muscular stresses and assisting in apposition of valve leaflets.

FIG. 6 shows an embodiment of a device according to the present invention that would alleviate this rotation phenomenon. FIG. 6 shows an accessory splint 70 connected to the superior-most ventricular splint 14 by a connecting bar 60. Accessory splint 70 and connecting bar 60 preferably are placed at approximately the same level along the ventricular wall as splint 14. Splint 14 preferably is positioned near to, and in this case medial to, the anterior papillary muscle PM. Accessory splint 70 then is positioned through the septum S, across the left ventricle LV, and through the ventricular free wall between the papillary muscles PM, similar to MV splint 20 described in connection with FIGS. 3a and 3b but at about the same level as the superior splint 14.

Connecting bar 60 attaches to the ends of tension members 16 and 72 at their left ventricular "free wall" ends. Both tension members 16 and 72 are tensioned, pressing connecting bar 60 into the left ventricle and effecting shape change to the ventricle and the mitral valve annulus. Connecting bar 60 prevents rotation of the left ventricle LV in the region of the anterior papillary muscle PM and causes uniform tensioning of the chordae associated with that papillary muscle PM and any associated ventricular wall. This is believed to lessen any degradation in MVR, and potentially improve the MVR, because the papillary muscles PM are brought to a more desired position, with less rotation, particularly as to the anterior papillary muscle.

The embodiments of the present invention described in connection with FIGS. 2a to 6 have been described in connection with the use of transventricular splints used to geometrically reshape a chamber of the heart and thereby lessen heart wall stresses and reduce dilatation. While the devices and related methods described herein would further benefit the ventricular splinting procedure and its effects, the devices and related methods of the present invention may be used independent of the ventricular splinting to improve dilatation and instead be used for repairing heart valves, and particularly mitral valves, without the use of adjunctive ventricular splints. For example, a mitral valve splint such as that shown in FIGS. 3a, 3b, and 3c could be utilized without additional ventricular shape change splints.

Figure 7:
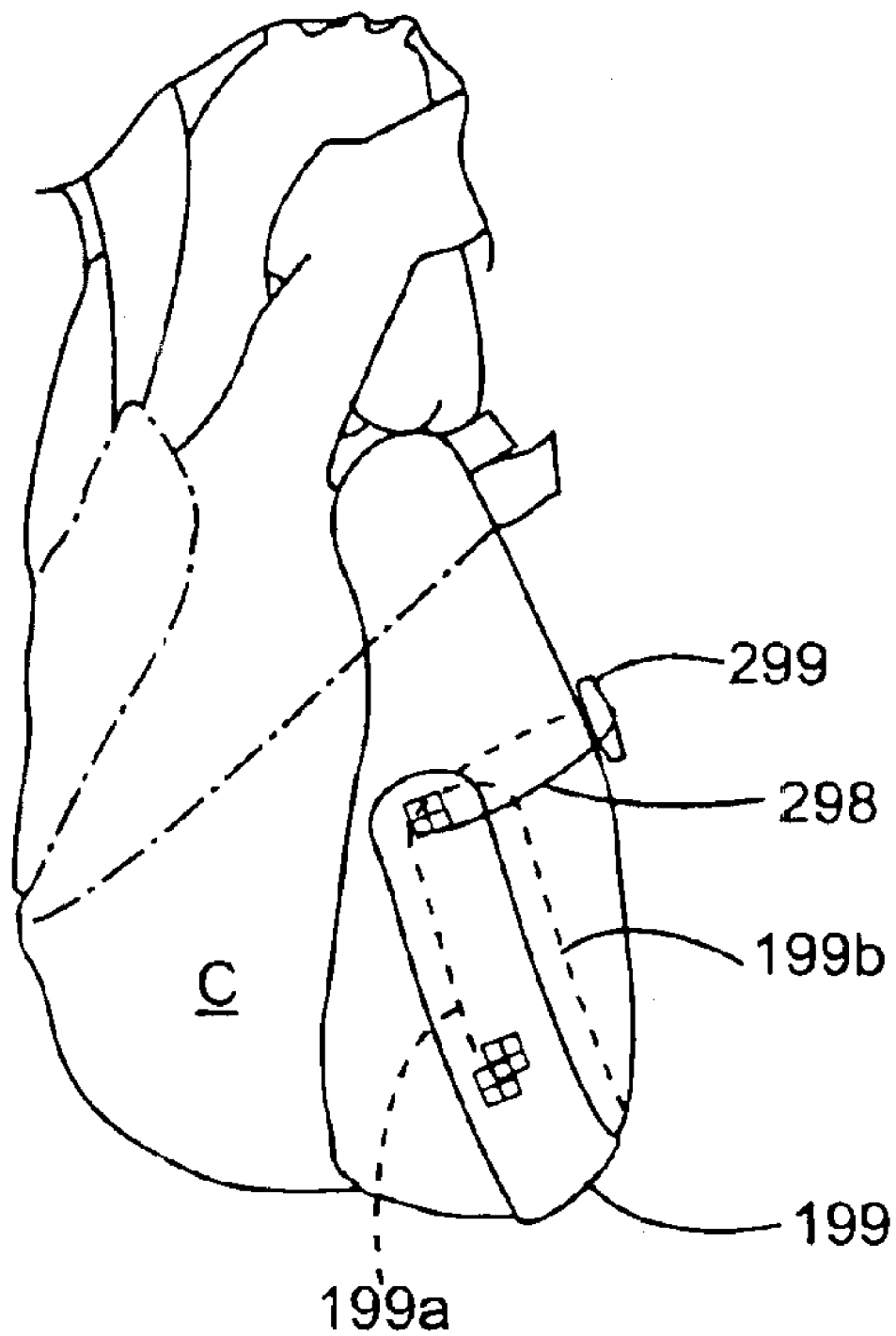
FIG. 7 is a perspective view of a heart with an external splint device and mitral valve anchor assembly and connecting mechanism disposed relative to the left ventricle to alter the shape of the left ventricle and to assist in apposition of valve leaflets according to an embodiment of the present invention.

Moreover, while many of the embodiments of the present invention have been described in connection with modifications to transventricular splinting structures, the same or similar modifications may be made to external-type devices for causing ventricular shape change. Examples of such external devices are shown in co-pending U.S. patent application Ser. No. 09/157,486 ("the '486 application") filed Sep. 21, 1998 and entitled "External Stress Reduction Device and Method," the complete disclosure of which is incorporated by reference herein. Modifying those external devices in a similar manner as with the transventricular splints will achieve beneficial impacts to the mitral valve function. For example, the accessory anchor pad shown in FIGS. 5a and 5b could be utilized in conjunction with an external stress reduction device, as shown, for example, in FIG. 7. In FIG. 7, an external splint 199 having a generally U-shaped configuration and including an anterior arm 199a and a posterior arm 199b, is positioned with respect to the left ventricle to create a substantially bi-lobed shape. In a preferred embodiment, the U-shaped external splint is made from a material that permits the splint to elastically deform under operationalloads and also from a material that is biocompatible. Examples of preferred materials include e-PTFE, or a polyester such as Dacron, for example. Such a splint, as well as other suitable external splints, is described in more detail in the '486 application incorporated above. As shown in FIG. 7, a runner 298, similar to the runner described with reference to FIGS. 5a and 5b, attaches at its ends to the arms 199a, 199b. An accessory anchor pad 299, also similar to the accessory anchor assembly discussed with reference to FIGS. 5a and 5b, attaches to the connecting runner 298. The runner 298 and accesory anchor pad 299 are positioned with respect to the heart so as to alter the shape of the mitral valve annuls to assist in coaptation of the valve leaflets. Alternatively, the runner and accessory anchor pad could be positioned so as to provide a repositioning of the papillary muscles, also to assist in coaptation of the valve leaflets.

It will be apparent to those skilled in the art that various modifications and variations can be made in the devices and related methods for improving mitral valve function of the present invention and in construction of such devices without departing from the scope or spirit of the invention. As an example, a combination of devices depicted above may be used for achieving improved mitral valve function. In one such combination, an accessory splint such as MV splint 20 shown in FIGS. 3a and 3b may include an anchor assembly 28 as shown in FIG. 4 and/or an accesory anchor pad structure 40 or 50 shown in FIGS. 5a and 5b. Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A method for improving the function of a valve of a heart, comprising:

placing a device relative to the heart so as to contact cardiac structure other than structure of the valve and so as to alter a shape of the valve;

real-time monitoring valve function; and adjusting the device relative to the heart based on data obtained during the adjusting from the real-time monitoring of valve function, wherein the real-time monitoring includes ultrasound imaging the valve.

2. The method of claim 1, wherein the device is a splint.

3. The method of claim 1, wherein the device is a splint and adjusting the splint includes changing a distance between at least two portions of the splint that contact respective portions of the heart.

4. The method of claim 1, further comprising deforming a wall of the heart and real-time monitoring valve function during the deforming.

5. The method of claim 4, wherein deforming the wall includes deforming the wall via a probe device.

6. The method of claim 4, further comprising positioning the device relative to the heart based on the real-time monitoring of valve function during the deforming.

7. The method of claim 1, further comprising positioning the device relative to the heart based on the real-time monitoring of valve function.

8. A method for improving the function of a valve of a heart, comprising:

placing a device relative to the heart such that at least part of the device is external to the heart and such that the device alters a shape of the valve;

real-time monitoring valve function; and adjusting the device relative to the heart based on data obtained during the adjusting from the real-time monitoring of valve function, wherein the real-time monitoring includes ultrasound imaging the valve.

9. The method of claim 8, wherein the device is a splint.

10. The method of claim 8, wherein the device is a splint and adjusting the splint includes changing a distance between at least two portions of the splint that contact respective portions of the heart.

11. The method of claim 8, further comprising deforming a wall of the heart and real-time monitoring valve function during the deforming.

12. The method of claim 11, wherein deforming the wall includes deforming the wall via a probe device.

13. The method of claim 11, further comprising positioning the device relative to the heart based on the real-time monitoring of valve function during the deforming.

14. The method of claim 8, further comprising positioning the device relative to the heart based on the real-time monitoring of valve function.

* * * * *